US00PP15593P2

(12) United States Plant Patent
Pellet

(10) Patent No.: US PP15,593 P2
(45) Date of Patent: Feb. 22, 2005

(54) FREEMAN MAPLE TREE NAMED 'AF#1'

(50) Latin Name: *Acer×freemanii*
Varietal Denomination: AF#1

(76) Inventor: Harold M. Pellet, Landscape Plant Development Center, 600 Arboretum Blvd., Excelsior, MN (US) 55331

( * ) Notice: Subject to any disclaimer, the term of this patent is extended or adjusted under 35 U.S.C. 154(b) by 0 days.

(21) Appl. No.: 10/350,432

(22) Filed: Jan. 24, 2003

Related U.S. Application Data

(60) Provisional application No. 60/351,344, filed on Jan. 24, 2002.

(51) Int. Cl.[7] ..... A01H 5/00
(52) U.S. Cl. ..... Plt./224
(58) Field of Search ..... Plt./224

*Primary Examiner*—Anne Marie Grunberg
(74) *Attorney, Agent, or Firm*—Penny Aguirre

(57) ABSTRACT

A new and distinct cultivar of *Acer×freemanii* named 'AF#1' is described. 'AF#1' is characterized by superior fall coloration.

2 Drawing Sheets

Botanical classification: *Acer×freemanii.*
Varietal denomination: 'AF#1'.

BACKGROUND

Maple trees belong to a genus (*Acer*) that contains approximately 150 species of evergreen and deciduous trees and shrubs that come in a wide range of sizes and shapes. The red maple (*Acer rubrum*) is widely used for street and ornamental plantings due to its beautiful fall color (yellow to red) and tolerance to compacted soils. The silver maple (*Acer saccharinum*) is a very large spreading tree that is very fast growing and tolerant of a wide range of cultural conditions. An interspecific hybrid between silver and red maple (the Freeman maple) generally combines the aesthetic qualities of the red maple with the greater tolerance to cultural conditions of the silver maple. Freeman maples reach a height of 40–60 feet and a width of 20–40 feet, have yellow to red flowers in early spring, and yellow to red fall color.

SUMMARY

'AF#1' is a new variety of *Acer×freemanii* (Freeman maple) that exhibits the following combination of characteristics: 1) Superior fall leaf coloration; 2) Leaves with sinuses that are more deeply cut than other Freeman maples; 3) Rapid growth; and 4) Early hardening in fall.

The new variety of *Acer×freemanii* (Freeman maple) was developed by crossing *Acer saccharinum* 'Beebe' (unpatented) and *Acer rubrum* 'Autumn Spire' (U.S. Plant Pat. No. 7,803). The resulting hybrid seedlings were grown in research plots at the University of Minnesota Horticultural Research Center, Excelsior, Minn. AF#1 was selected from the progeny of the cross, based on its superior fall coloration and plant form.

'AF#1' was first asexually reproduced by softwood cuttings at the University of Minnesota Horticultural Research Center, Excelsior, Minn. Asexual propagation results in plants that are stable and reproduced true to type in successive generations.

The fall coloration of 'AF#1' has been superior in each year of observation. Typical fall leaf coloration is RHS 180A, ranging from RHS 46A to RHS 179B. In comparison, 'Autumn Spire' exhibits fall leaf coloration of RHS 46A (see FIG. 1). Alphanumeric color designations refer to values based on The R.H.S. Colour Chart published by The Royal Horticultural Society, London, England. Colours for 'AF#1' are based on the 1995 edition of the R.H.S. chart, while colors for 'Autumn Spire' are based on the 1966 edition.

DESCRIPTION OF DRAWINGS

The accompanying color photographs show characteristics of 13 year-old trees of 'AF#1' grown under typical field conditions in full sun without supplementary water in a research field in Excelsior Minn. The photographs depict color features as true as is reasonably possible.

DETAILED DESCRIPTION

The following data pertain to 13 year-old trees grown at the University of Minnesota Horticultural Research Center, Excelsior, Minn. When dimensions, sizes, colors and other characteristics are given, it is to be understood that such characteristics are approximations set forth as accurately as possible. Variations of the usual magnitude incident to climatic factors, fertilization, pruning, pest control and other cultural practices are to be expected.

Botanical classification: *Acer×freemanii,* AF#1.
Plant:

*Growth habit.*—Growth habit of young tree is oval, becoming more rounded with age. Branches arise from the main trunk at approximately a 45° angle. Trees are very symmetrical.

*Size.*—This selection has a rapid rate of growth. A two-year old branched AF#1 tree reached a caliper of approximately 5–6" and a height of approximately 20' in six years.

*Bark.*—Smooth on young trees with an RHS color 201D.

*Presence of lenticels.*—White lenticels, 0.5 to 2.0 mm in length, are present on current year's growth.

*Branch spacing.*—Primary lateral branches are distributed around the main trunk at a vertical spacing of 12–20 cm.

*Branch length.*—Primary lateral branches on the lower third of the crown range in length from 2.5 to 13 m. Secondary branches on this portion of the crown range in length from 0.1 to 1.7 m. Lengths of primary and secondary laterals decrease nearer to apex of main trunk. Predicted branch length at maturity is comparable to that of other Freeman maples.

*Branch diameter.*—Diameter of primary lateral branches on lower third of crown range in size from 4.0 to 7.5 cm. Secondary branches range in diameter from 0.2 to 2.8 cm. Diameters of primary and secondary laterals decrease nearer to apex of main trunk. Predicted branch diameter at maturity is comparable to that of other Freeman maples.

Figure 1:
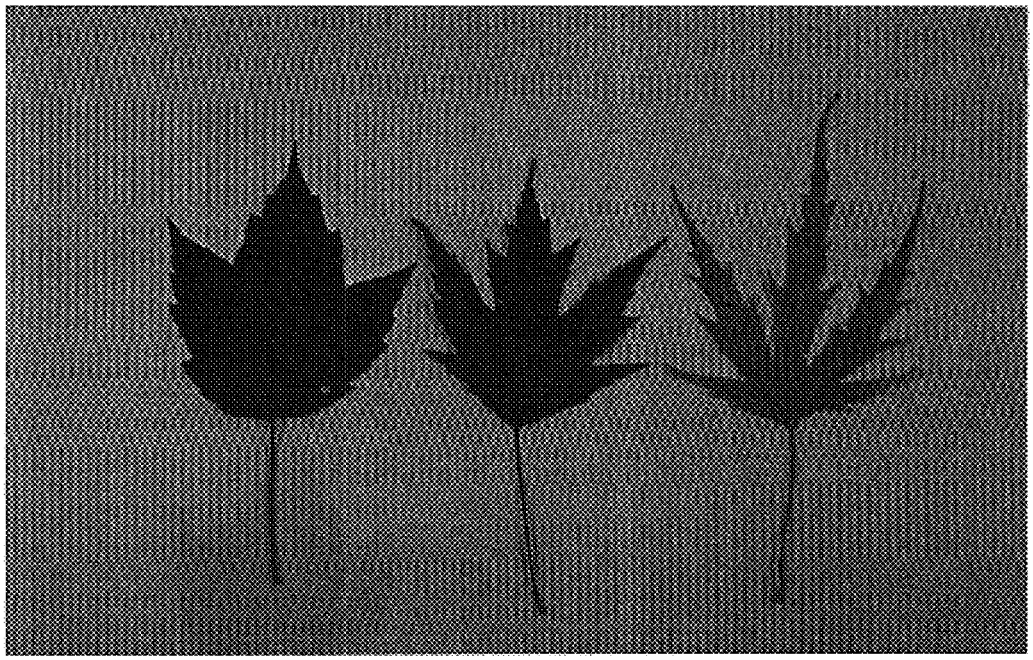
FIG. 1 is a photograph illustrating the fall color of leaves from *Acer rubrum* 'Autumn Spire' (left), 'AF#1' (center), and *Acer saccharinum* 'Beebe' (right).
Figure 2:
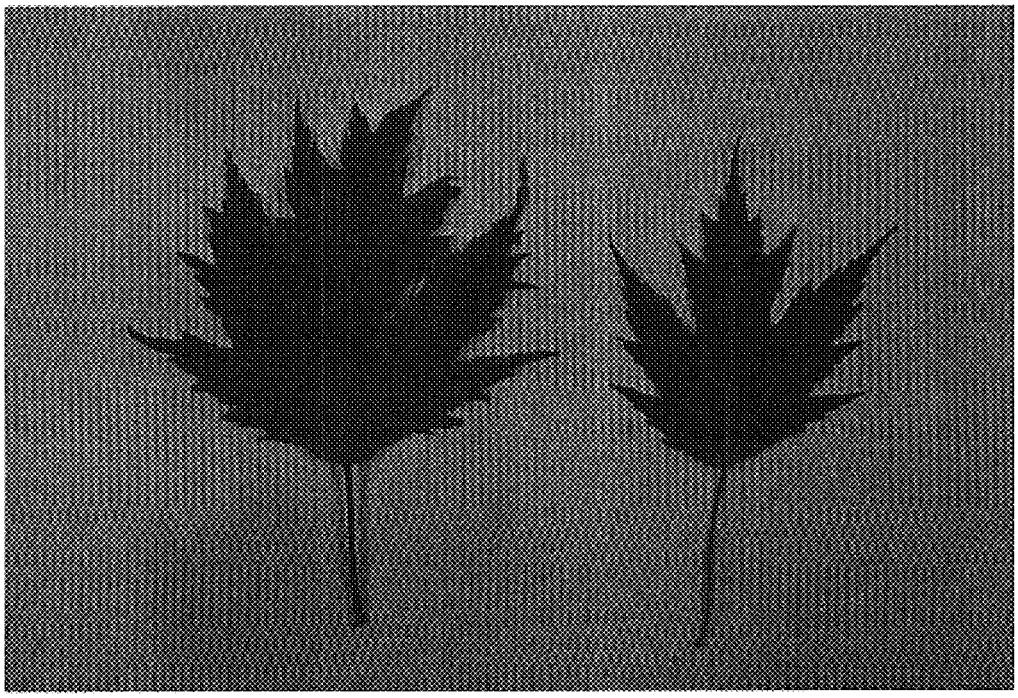
FIG. 2 is a photograph illustrating juvenile (left) and mature (right) leaf shape of 'AF#1.'

Foliage:

*Shape.*—Opposite leaves are deeply lobed to cleft with three distinct lobes and two smaller lobes at the base. Margins are serrate to double-serrate, apex is acuminate, base is acute, and venation is palmate. Sinuses are irregular, ranging from lobed to cleft. Juvenile growth is noticeably different from mature growth, with leaves appearing ruffled and having a wider sinus than mature growth (see FIG. 2).

Figure 3:
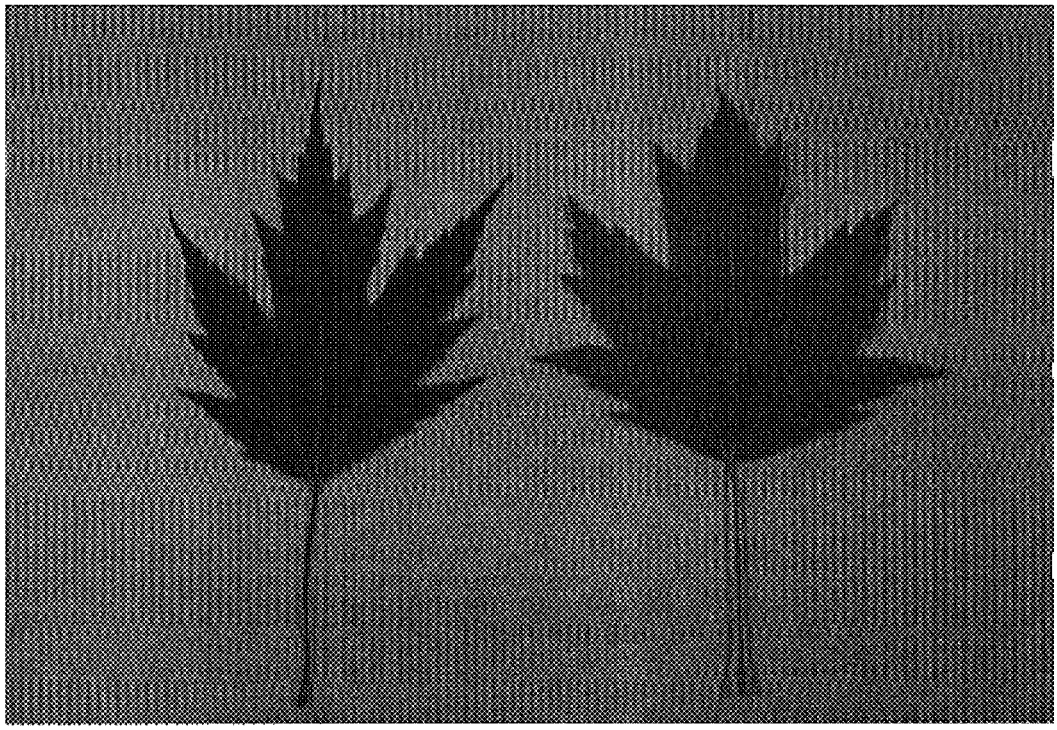
FIG. 3 is a photograph illustrating leaf color of the upper leaf surface (left) and lower leaf surface (right) of 'AF#1.'
Figure 4:
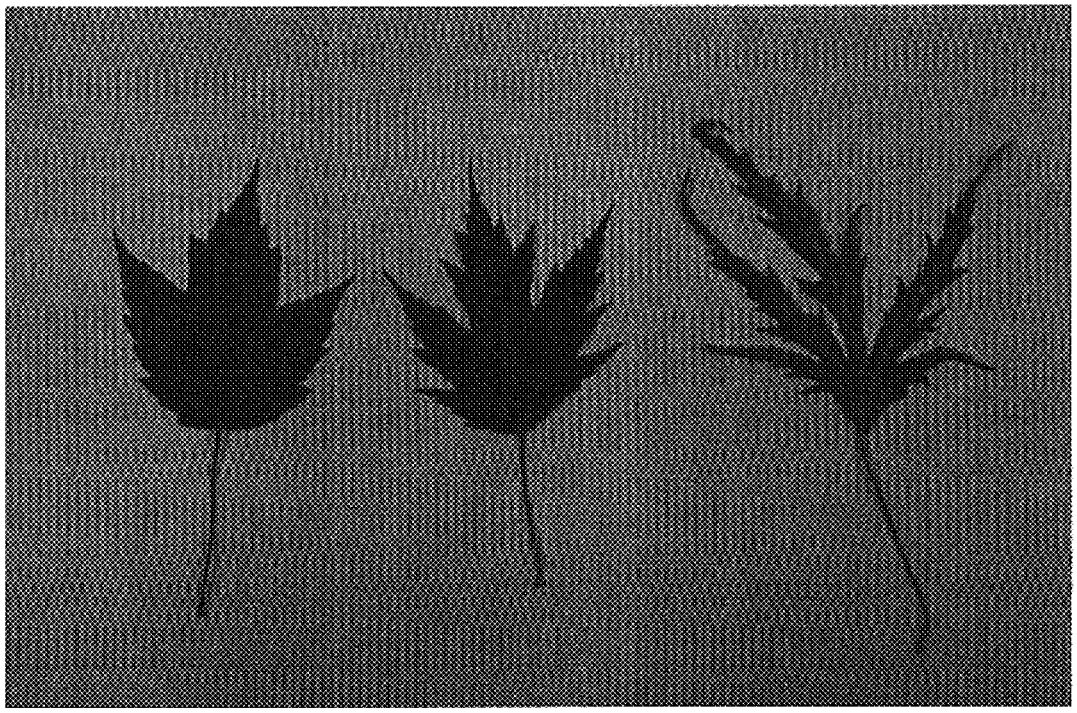
FIG. 4 is a photograph illustrating the summer color of leaves from *Acer rubrum* 'Autumn Spire' (left), 'AF#1' (center), and *Acer saccharinum* 'Beebe' (right).

*Color.*—During the summer, upper surface is RHS 147A and lower surface is RHS 191B (see FIG. 3). During the fall, AF#1 produces coloration of RHS 180A, ranging from 46A to 179B.

*Size.*—Leaves average 12.7 cm in length (range 11.5 to 14 cm) and 12.2 cm in width (range 11.0 to 13.5 cm).

*Leaf surface.*—Upper and lower surfaces are glabrous.

*Petiole length.*—Average petiole length is 8.5 cm.

*Petiole color.*—Upper surface of petioles is greyed-red (RHS 180B) while the lower surface is yellow-green (RHS 144C).

*Vegetative bud size.*—Vegetative buds vary in length from 0.1 to 0.4 cm and 0.2 to 0.3 cm across at the widest point.

*Vegetative bud shape.*—Flattened, ovoid with imbricate bud scales.

*Vegetative bud color.*—In June, the base of the vegetative buds that is enclosed by the petiole is yellow-green (RHS 144C) while the exposed bud apex is rosy red (RHS 53D).

Flowers and reproductive organs:

*Flowers.*—Flowers are typical of other male selections of Freeman Maples. Flowers open from Globose-shaped buds and are arranged in dense, compact clusters emerging from previous years growth. Flowers are red in color and open in early spring before the leaves emerge. Individual flowers are 5-merous with stamens (most likely 8) that are reddish-brown in color and exserted. Pollen has not been observed.

*Seeds.*—'AF#1' possesses only male flowers and therefore, does not produce seeds.

Development and culture:

*Hardiness.*—Hardy to U.S.D.A. hardiness zone 3B. 'AF#1' hardens earlier than other cultivars of Freeman maples. In laboratory determinations in mid-November, 'AF#1' survived to −37° C., while 'Autumn Blaze' (U.S. Plant Pat. No. 4,864) and 'Celzam' (U.S. Plant Pat. No. 7,279) survived to −31° C. and −34° C., respectively.

*Disease resistance.*—No serious disease problems have been observed.

What is claimed is:

1. A new and distinct *Acer×freemanii* plant named 'AF#1', as illustrated and described herein.

* * * * *

UNITED STATES PATENT AND TRADEMARK OFFICE

CERTIFICATE OF CORRECTION

PATENT NO. : PP 15,593 P2 
DATED : February 22, 2005
INVENTOR(S) : Harold M. Pellett and Steven T. McNamara It is certified that error appears in the above-identified patent and that said Letters Patent is hereby corrected as shown below:

Title page,
Item [76], Inventors, correct the spelling of the first inventor to -- Harold M. Pellett --; and add second inventor -- Steven T. McNamara, MN Landscape Arboretum, 600 Arboretum Blvd., Excelsior, MN 55331 --

Signed and Sealed this

Seventh Day of June, 2005

JON W. DUDAS
*Director of the United States Patent and Trademark Office*

UNITED STATES PATENT AND TRADEMARK OFFICE

CERTIFICATE OF CORRECTION

PATENT NO. : PP15,593 P2
APPLICATION NO. : 10/350432
DATED : February 22, 2005
INVENTOR(S) : Harold M. Pellett and Steven T. McNamara It is certified that error appears in the above-identified patent and that said Letters Patent is hereby corrected as shown below:

On the title page insert item (73) -- Regents of the University of Minnesota, Minneapolis Minnesota --

Signed and Sealed this

Fifth Day of September, 2006

JON W. DUDAS
*Director of the United States Patent and Trademark Office*